(12) United States Patent
Anderson et al.

(10) Patent No.: US 7,491,382 B2
(45) Date of Patent: Feb. 17, 2009

(54) HAIR AND SCALP COMPOSITION WITH A CROSSLINKED SILICONE ELASTOMER AND METHOD OF USING SAME

(75) Inventors: Glen T. Anderson, Pleasantville, NY (US); Clifford A. Milow, Massapequa Park, NY (US); Xiaochun Luo, New City, NY (US)

(73) Assignee: Avon Products, Inc., New York, NY (US)

( * ) Notice: Subject to any disclaimer, the term of this patent is extended or adjusted under 35 U.S.C. 154(b) by 0 days.

(21) Appl. No.: 11/862,689

(22) Filed: Sep. 27, 2007

(65) Prior Publication Data

US 2008/0014165 A1      Jan. 17, 2008

Related U.S. Application Data

(63) Continuation of application No. 10/334,493, filed on Dec. 31, 2002, now abandoned.

(51) Int. Cl.
*A61Q 5/02* (2006.01)

(52) U.S. Cl. .................... 424/70.12; 424/70.1

(58) Field of Classification Search ........ None
See application file for complete search history.

(56) References Cited

U.S. PATENT DOCUMENTS 5,871,761 A * 2/1999 Kuwata et al. ............ 424/401

2001/0018432 A1    8/2001 Singleton et al.

FOREIGN PATENT DOCUMENTS

WO      WO 03/004977 A2     6/2003

OTHER PUBLICATIONS

XP002220204, KR, Jan. 1, 1997, Hankook Cosmetics Co., Ltd., Abstract.
Database WPI Week 199805, Thompson Scientific, London, GB: AN, 1998-046901, XP002490989 and JP 09 295920 A (Nipoon Gosei Gomu KK) Nov. 18, 1997, abstract.

* cited by examiner

*Primary Examiner*—Jyothsna A Venkat
(74) *Attorney, Agent, or Firm*—Joan M. McGillycuddy; Charles J. Zeller; Anthony M. Santini

(57) ABSTRACT

The present invention provides a water-based composition comprising a non-emulsifying crosslinked silicone elastomer in an amount effective to decrease the amount of sebum on the hair or scalp. The water-based compositions of the present invention are in non-emulsion form. More preferably, the water-based compositions of the present invention have a suspending agent in an amount effective to suspend the crosslinked silicone elastomer within the water-based composition. The present invention also provides to a method of method for absorbing and/or removing sebum and/or styling product residue from the hair or scalp. The method comprises the step of applying the water-based composition to the hair and/or scalp. Preferably, the water-based hair composition is distributed through the hair and/or scalp, e.g., by using a comb or brush.

7 Claims, No Drawings

HAIR AND SCALP COMPOSITION WITH A CROSSLINKED SILICONE ELASTOMER AND METHOD OF USING SAME

This is a continuation of application Ser. No. 10/334,493, filed Dec. 31, 2002 now abandoned.

BACKGROUND OF THE INVENTION

1. Field of the Invention

The present invention relates to a hair composition, in particular to a non-rinse-off, i.e., leave-on, composition. More particularly, the present invention relates to non-rinse-off water-based composition that includes a crosslinked silicone elastomer. The present invention also relates to a method for using a composition for absorbing and/or removing sebum or styling product residue from the hair or scalp, most preferably, without the requirement of rinsing off the product.

2. Description of the Related Art

Human hair, in common with other parts of the body, becomes soiled and requires cleaning or shampooing. Personal habits of hair care vary greatly but, in general, people shampoo their hair at various intervals of a day to a week or two apart. However, there are times during the between-shampoo intervals where people would like to refresh their hair by decreasing oil, sebum and/or the odor associated with sebum. This is especially true in this time when busy business workers use work break times to attend fitness clubs or during the warmer months. Both consumers and those skilled in the art have recognized a need for an in-between hair cleaning means that is simpler, faster and more convenient than shampooing.

Crosslinked silicone elastomers are known to provide conditioning benefits to the hair, such as improving combability and leaving a soft and silky feel. However, heretofor crosslinked silicone elastomers have generally been incorporated into rinseoff compositions, such as shampoos or conditioners, or anhydrous compositions. For example, EP 855178 A2 discloses wash-off hair care products that include alpha-hydroxycarboxylic acids and water-insoluble silicone elastomer powders. In addition, the examples of the EP 855178 have greater than 6 wt % oil soluble ingredients.

However, for hair care formulations, especially leave-on/non-rinse-off compositions, it is desirable to use an aqueous based system instead of an emulsion or an anhydrous system. Although an anhydrous system can effectively solubilize and deposit the crosslinked silicone elastomer on the hair, the solvents present in such anhydrous system leave greasy, oily undesirable residue behind on the hair and scalp. In addition, the crosslinked silicone elastomer has a tendency to absorb the oil/solvent present in such systems. As a result, the crosslinked silicone elastomer is less able to absorb sebum from the hair/scalp. Anhydrous formulas as such are also much more expensive, since they contain no water. Even alcohol-based anhydrous formulations, which are fairly affordable, are not possible due to the insolubility of crosslinked silicone elastomers in alcohol.

Emulsion systems can be and have been used to solubilize silicone elastomers in hair care formulations. However, high levels of emulsifiers and/or surfactants are needed to stabilize such systems. The emulsifiers/surfactants when used in high levels are also left behind on the hair, leaving a greasy feel similar to the anhydrous systems discussed above. U.S. Pat. No. 6,346,583 discloses hair care compositions that include a crosslinked silicone elastomer that has emulsifying properties.

U.S. Pat. No. 4,764,363 discloses hair styling mousse compositions. The '363 mousse compositions include a silicone emulsion that has a continuous water phase in which there is a dispersed phase that comprises an anionically stabilized hydroxylated polyorganosiloxane, a colloidal silica and a catalyst.

The present invention overcomes the deficiencies and disadvantages of the prior art.

SUMMARY

The present invention relates to a water-based composition comprising a non-emulsifying crosslinked silicone elastomer in an amount effective to decrease the amount of sebum on the hair or scalp. The water-based compositions of the present invention are in non-emulsion form. More preferably, the water-based compositions of the present invention have a suspending agent in an amount effective to suspend the crosslinked silicone elastomer within the water-based composition. The water-based compositions of the present invention also preferably have less than about 5 wt % oil ingredients.

The present invention also relates to a method of absorbing and/or removing sebum and/or styling product residue from the hair or scalp. The method comprises the step of applying the water-based composition to the hair and/or scalp. Preferably, the water-based hair composition is distributed through the hair and/or scalp, e.g., by using a comb or brush.

DETAILED DESCRIPTION OF THE INVENTION

This invention relates to an aqueous hair care composition and method for absorbing and/or removing sebum from oily hair. The composition is sprayed onto the hair and preferably combed through, whereby the perception of greasiness on the hair is dramatically reduced.

Crosslinked Silicone Elastomer

The hair composition has a non-emulsifying crosslinked silicone elastomer (hereinafter "crosslinked silicone elastomer"). An elastomer is generally a chain polymer having a degree of crosslinking sufficient to provide a rubberlike consistency. A crosslinked silicone elastomer is formed from a siloxane polymer having at least two free reactive groups preferably bonded to at least one terminal silicon atom. The reactive groups can include, but are not limited to, vinyl, allyl or epoxide moieties. The groups then react with Si—H linkages of another suitable polysiloxane backbone capable of participation in an addition reaction, such as a molecularly spherical MQ resin. The reaction results in a three-dimensional crosslinked polymer. The crosslinked silicone elastomer is essentially non-emulsifying (e.g., polyoxyalkylene groups absent). The average molecular weight of the crosslinked silicone elastomer preferably ranges from about 2,000 to about 20 million, most preferably from about 1 million to about 20 million.

Examples of crosslinked silicone elastomers suitable for use in the present compositions include, but are not limited to, one or more dimethicone crosspolymers, such as DC 9040 of Dow Corning Corp.; organopolysiloxanes (a.k.a. polysilicone-11), such as GRANSIL GCM and GRANSIL SR-5CYC of Grant Industries; dimethicone/vinyl dimethicone crosspolymers, such as SFE839 of General Electric, KSG15 of Shin-Etsu, and DC 9509 of Dow Corning Corp.; or any combinations thereof. Dimethicone/vinyl dimethicone crosspolymers for use in the present compositions include those disclosed in U.S. Pat. Nos. 5,871,761 and 6,013,682, which are incorporated herein by reference. Most preferred examples of such useful crosslinked silicone elastomers are those provided in the form of non-ionic suspensions (for example, DC 9509 SILICONE ELASTOMER SUSPENSION of Dow Corning Corp.) or non-ionic emulsions (for example, DC HMW 2220 NON-IONIC EMULSION of Dow Corning Corp.).

It is preferred that the crosslinked silicone elastomer is solid. By the term "solid" it is meant that the crosslinked silicone elastomer does not flow or have a viscosity as do silicone fluids. DC 9509 from Dow Corning Corp., discussed above, is an example of such a solid crosslinked silicone elastomer.

Although crosslinked silicone elastomers can be added directly to the hair composition, it is preferred that the crosslinked silicone elastomer is added to the hair composition in the form of a pre-solubilized/pre-dispersed suspension or emulsion. When such a predispersed crosslinked silicone elastomer is used, as is most preferred, the amount of emulsifier/surfactant in the crosslinked silicone elastomer dispersion will be calculated as part of the level of emulsifier/surfactant contained in the overall hair care composition, as will be discussed further below.

The crosslinked silicone elastomer is present in the hair composition in an amount effective to decrease sebum on the hair or scalp as compared to a composition without the crosslinked silicone elastomer. Preferably, the crosslinked silicone elastomer is present at about 0.01 wt % to about 10 wt %, based on the total weight of the composition. More preferably, the crosslinked silicone elastomer is present at about 0.1 wt % to about 5 wt %, based on the total weight of the composition. Most preferably, the crosslinked silicone elastomer is present at about 0.5 wt % to about 2.5 wt %, based on the total weight of the composition.

Water

The present invention uses a water-based system. A water-based system according to the present invention is a system that is has an aqueous phase that contains water and those ingredients that are freely soluble in water. Preferably, the compositions of the present invention include at least about 20 wt %, more preferably at least about 40 wt %, most preferably at least about 50 wt %, water based on the total weight of the hair composition. Most preferably, the hair care composition includes at least about 75 wt % water, based on the total weight of the hair composition.

Suspending Agent

Because the crosslinked silicone elastomer is oil soluble and thus water insoluble, it is preferred the composition includes a suspending agent. In prior art emulsion systems, the crosslinked silicone elastomer was simply added to the oil phase, which was later emulsified. In the water-based systems of the present invention, the crosslinked silicone elastomer, because it is non-hydrophilic and non-emulsifying in nature, may form a separate layer over time. Although this does not eviscerate the advantages of the present invention since the composition may be shaken prior to use to redisperse the crosslinked silicone elastomer, it is more preferred that the crosslinked silicone elastomer remains suspended through the product life. Thus, to improve the stability of the water-based system of the present invention, the composition preferably includes a suspending agent in an amount sufficient to disperse/suspend the crosslinked silicone elastomer within the composition for a period of time greater than three months.

Examples of suspending agents include, but are not limited to, clays (e.g., bentonite, smectite, hectorite, kaolin and montmorillonite), metal silicates (e.g., magnesium aluminum silicate, calcium silicate and aluminum silicate), polyacrylamide, long chain acyl derivatives (e.g., glycol esters of fatty acids, alkanol amides of fatty acids, and amine oxides of fatty acids), acrylics (e.g., carbomers, acrylate polymers, polyacrylates and co-polymers), urethanes and polyurethanes, polyesters, polysaccharides (e.g., cellulosics, xanthan gum), polyolefins, polyamides, polyimides, polyethylenes and other polyalkyls, polyols, polystyrenes, polyethers, polyhalides, polynitriles, proteins, triglycerides, polyamino acids, silicone polymers and resins, esters derived from rosin, epoxy resins, shellacs and latexes. Particularly preferred suspending agents are acrylates/C10-30 alkyl acrylate crosspolymer, commercially available from Noveon, Inc. as PEMULEN TR-1 AND PEMULEN TR-2. Mixtures of two or more suspending agents is also contemplated.

The amount of suspending agent can be adjusted using standard empirical routines for optimization, as is well understood in the art. Factors to be considered include, but are not limited to, the specific type and amount of crosslinked silicone elastomer(s) being used, the amount of water in the composition, the type and amount of emulsifier(s) being used to pre-disperse the crosslinked silicone elastomer, if the formulation includes alcohol and in what amount, the amount and type of other hydrophilic ingredients, such as glycols or polyols, and the type and amount of preservatives or fragrances that may be added. It is preferred that the suspending agent is present from about 0.01 wt. % to about 10.0 wt. %, more preferably from about 0.025 wt. % to about 2.5 wt. % and most preferably from about 0.05 wt. % to about 0.75 wt. %, based upon the total weight of the composition.

Emulsifer/Surfactants

Because the compositions of the present invention are in non-emulsion form, the compositions are substantially free of emulsifiers/surfactants. Emulsifier/surfactant may be added as long as the composition remains in a non-emulsion form. The amount of emulsifer/surfactant that can be added without forming an emulsion can be adjusted using standard empirical routines for optimization, as is well understood in the air. Factors to be considered include, but are not limited to, the specific type and amount of crosslinked silicone elastomer(s) being used, the amount of water in the composition, the amount of water in the composition, the type and amount of emulsifier(s) being used to pre-disperse the crosslinked silicone elastomer, if the formulation includes alcohol and in what amount, the amount and type of other hydrophilic ingredients, such as glycols or polyols, and the type and amount of preservatives or fragrances that may be added. For guidance, the compositions of the present invention preferably have less than about 1 wt % emulsifer and/or surfactant, and more preferably less than 0.5 wt. % emulsifer/surfactant. In a preferred embodiment of the hair composition, emulsifiers/surfactants are present in amount less than about 1.0 wt %, and the oil-soluble ingredients (discussed below) are present in an amount less than about 5.0 wt %, based oil the total weight of the hair composition.

Since it is most preferred that the crosslinked silicone elastomer is predispersed prior to being added to the composition (as discussed in the crosslinked silicone elastomer section above), the contribution of the amount of emulsifier/surfactant in the crosslinked silicone elastomer predispersion is considered when calculating the total amount of emulsifier/surfactant in the overall composition.

Non Emulsion Form

The hair composition is aqueous but in a form other than an emulsion, i.e., the hair composition is substantially free of emulsion form or structure. Suitable composition forms include dispersions and suspensions.

Oil Soluble Ingredients

Since the purpose of the compositions of the present invention is to absorb sebum and other oils, it is preferred that the compositions are substantially free of oil-soluble ingredients (other than the crosslinked silicone elastomer). Oil-soluble ingredients diminish the effectiveness of the crosslinked silicone elastomer since the crosslinked silicone elastomer will absorb the oil-soluble ingredient in the composition, thus have a lower capacity for absorbing the sebum from hair/scalp. Preferably, compositions of the present invention have less than 5 wt %, more preferably less than 2.5 wt %, most preferably less than 1 wt % oil-soluble ingredients. For calculation purposes, the crosslinked silicone elastomer is not considered an oil soluble ingredients, and is considered only for its contribution to the total weight of the composition.

Optional Ingredients

Compositions of the present invention may also contain one or more additional ingredients conventionally incorporated into hair care compositions. Such additional ingredients include styling agents, such as resins and hair-setting polymers, perfumes, dyes, buffering or pH adjusting agents, viscosity modifiers, opacifiers, pearlizers, preservatives, antibacterial agents, antidandruff agents, vitamins, foam boosters, proteins, moisturizing agents, herb or other plant extracts, or other natural ingredients. The compositions of the present invention may include one or more additional components, such as one or more antimicrobials, antioxidants, buffering agents, chelating agents, colorants, conditioning agents, emollients, film formers, fragrances, humectants, lubricants, moisturizers, pigments, preservatives, skin penetration enhancers, stabilizers, vitamins, or any combinations thereof.

Product Forms

The compositions of the present invention may have a number of different product forms. Such suitable product forms include an aerosol or pump spray, mousse, foam, solution, serum, or the hair care composition may be incorporated into a towelette. Most preferably, the composition is in a product form that allows for easy transportation, access and use. Most preferably the product form is a sprayable (e.g., aerosol or pump sprays) solution. The compositions of the present invention may be incorporated into combs and brushes within a separate reservoir in the same manner used for dental care toothbrushes that dispense dentifrices and toothpastes. Examples of such systems are disclosed in U.S. Pat. Nos. 5,913,632; 5,882,134; 4,787,765; 6,206,600; and 6,257,791, the disclosures of which are incorporated by reference.

In preferred form, the present invention is provided in a small package that can be conveniently carried in a pocket, handbag or briefcase.

EXAMPLE 1

A hair composition according to the present invention may be made according to the following.

| Ingredient | | wt % |
|---|---|---|
| Dimethicone/Vinyl Dimethicone Crosspolymer suspension (with less | Crosslinked Silicone Elastomer | 2.0 |

-continued

| Ingredient | | wt % |
|---|---|---|
| than 20% emulsifier based upon the weight of the suspension) | | |
| Acrylates/C10-30 Alkyl Acrylate Crosspolymer | Suspending Agent | 0.25 |
| Disodium EDTA | Chelating Agent | 0.2 |
| Ethyl Alcohol | Volatile Solvent/Preservative | 10.0 |
| Methyl paraben | Preservative | 0.2 |
| Sodium Hydroxide | pH adjuster | 0.1 |
| Water | | QS |

Method of Use

The compositions of the present invention are applied to the hair and/or scalp between any two wash occasions. The method of using the compositions of the present invention include the step of applying the composition to the hair and/or scalp. Preferably, the composition is then distributed through the hair and/or over the scalp. The distribution may be accomplished using, for example, a brush, a comb or a plurality of fingers. When the composition is incorporated into a reservoir of a brush or comb, as described above, the steps of applying and distributing may occur simultaneously.

When practicing the preferred method of the present invention, the composition is applied to hair in between washes. Preferably, when the hair composition is applied to the hair or scalp has not been washed for at least 1 hour before, more preferably at least 2 hours before, and most preferably at least 4 hours before composition is applied.

The compositions of the present invention may also be used in a method of removing styling product buildup between washes. Just as the compositions of the present invention absorb sebum and/or oils from the hair, the compositions also assist in absorbing the heavy, oily ingredients often included in conventional styling products. To practice such a method, a composition of the present invention is applied to the hair and/or scalp. Preferably, the composition is then distributed through the hair and/or over the scalp. The distribution may be accomplished using, for example, a brush, a comb or a plurality of fingers. When the composition is incorporated into a reservoir of a brush or comb, as described above, the steps of applying and distributing may occur simultaneously.

It should be understood that the foregoing description is only illustrative of some embodiments of the present invention. Various alternatives and modifications can be devised by those skilled in the art without departing from the invention. Accordingly, the present invention is intended to embrace all such alternatives, modifications and variances that fall within the scope of the appended claims.

What is claimed is:

1. A method for decreasing the amount of sebum on the hair or scalp of a person with a leave-on, non-rinse-off hair care composition, comprising:
    (a) forming a non-emulsifying leave-on, non-rinse-off water-based hair care composition comprising:
        i) a non-viscous crosslinked silicone elastomer, wherein said non-viscous cross linked silicone elastomer is dimethicone/vinyl dimethicone crosspolymer in an amount of from about 0.01 wt % to about 10 wt % to deposit a sebum-absorbing level of said crosslinked silicone elastomer on the hair or scalp after the composition has been applied to the hair or scalp;

ii) a suspending agent selected from the group consisting of clays, metal silicate, xanthan gum and an acrylates/C10-30 alkyl acrylate crosspolymer in amount of from about 0.01 wt % to about 10 wt % to suspend said crosslinked silicone elastomer in said composition;
iii) a sufficient amount of water;
(b) applying the leave-on, non-rinse-off hair care composition to the hair or scalp of a person;
(c) distributing the hair care composition on the hair or scalp of a person with means selected from the group consisting of a brush, a comb, and by hand, whereby the perception of greasiness on the hair is substantially reduced, wherein the hair composition is selected from the group consisting of aerosol spray, pump spray, mousse, foam, solution serum, and towelette.

2. The method claim 1, wherein said hair or scalp has not been washed for a period of time greater than 1 hour before said applying of said water-based composition.

3. The method of claim 1, wherein said composition comprises from about 0.1 wt % to about 5 wt % of said crosslinked silicone elastomer.

4. The method claim 3, wherein said composition comprises from about 0.5 wt % to about 2.5 wt % of said crosslinked silicone elastomer.

5. The method of claim 1, wherein said suspending agent is in an amount sufficient to suspend said crosslinked silicone elastomer in said composition for at least three months.

6. The method of claim 1, wherein said composition comprises from about 0.05 wt % to about 0.75 wt % of said suspending agent.

7. The method of claim 1, wherein the hair composition is selected from the group consisting of aerosol spray and pump spray.

* * * * *